(12) United States Patent
Roninson et al.

(10) Patent No.: US 6,268,134 B1
(45) Date of Patent: *Jul. 31, 2001

(54) METHOD AND APPLICATIONS FOR EFFICIENT GENETIC SUPPRESSOR ELEMENTS

(75) Inventors: Igor B. Roninson, Wilmette; Tatyana Holzmayer, Chicago, both of IL (US); Choi Kyunghee, Denver, CO (US); Andrei Gudkov, Chicago, IL (US)

(73) Assignee: Board of Trustees of University of IL, Urbana, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/158,469

(22) Filed: Sep. 22, 1998

Related U.S. Application Data

(62) Division of application No. 08/039,385, filed on Sep. 7, 1993, now Pat. No. 5,811,234.

(51) Int. Cl.[7] .................................................. C12Q 1/68
(52) U.S. Cl. .......................... 435/6; 435/69.1; 435/91.1; 435/375; 536/24.5
(58) Field of Search .......................... 435/6, 69.1, 91.1, 435/375; 536/24.5

(56) References Cited

U.S. PATENT DOCUMENTS

| | | |
|---|---|---|
| 4,753,873 | 6/1988 | Beltz et al. . |
| 5,217,889 | 6/1993 | Roninson et al. . |
| 5,240,841 | 8/1993 | Johnston et al. . |
| 5,665,550 | 9/1997 | Roninson et al. . |
| 5,811,234 | 9/1998 | Roninson et al. . |

FOREIGN PATENT DOCUMENTS

| | | |
|---|---|---|
| WO 8803558 | 5/1988 | (WO) . |
| WO 9207071 | 4/1992 | (WO) . |

OTHER PUBLICATIONS

Baird et al., "Identification, cloning, and characterization of the *Escherichia coli* sohA gene, a suppressor of the htrA (degP) Null phenotype," *Journal of Bacteriology* 172(3):1587–1594 (Mar. 1990).
Baltimore et al., *Nature* 335:395–396 (1988).
Bunell et al., *Somat. Cell Mol. Genet.* 16:151–162 (1990).
Ch'ng et al., *Proc. Natl. Acad. Sci. USA* 86:10006–10010 (1989).
Chejanovsky et al., *J. Virol.* 64:1764–1770 (1990).
Chen et al., "Internal Duplication and Homology with Bacterial Transport Proteins in the mdr1 (P–Glycoprotein) Gene from Multidrug–Resistant Human Cells," *Cell* 47:381–389 (1986).
Daugherty et al., *Gene Anal. Tech.* 6:1–16 (1989).
Davis et al., *Microbiology* Harper and Row, Philadelphia, PA (1980).
Deiss et al., "A genetic tool used to identify thioredoxin as a mediator of a growth inhibitory signal," *Science* 252:117–252 (Apr. 5, 1991).
Friedman et al., "Expression of a truncated viral trans–activator selectively impedes lytic infection by its cognate virus," *Nature* 335:452–454 (Sep. 29, 1988).
Green et al., *Cell* 58:215–223 (1989).
Groger et al., "Directional antisense and sense cDNA cloning using Epstein–Barr virus episomal expression vectors," *Gene* 81:285–294 (1989).
Gudkov et al., "Isolation of genetic suppressor elements, inducing resistance to topoisomerse II–interactive cytotoxic drugs, from human topoisomerase II cDNA," *Proceedings of the National Academy of Sciences of USA* 90(8):3231–3235 (Apr. 15, 1993).
Herskowitz, "Functional inactivation of genes by dominant negative mutations," *Nature* 329:219–222 (1987).
Holzmayer et al., "Isolation of dominant negative mutants and inhibitory antisense RNA sequences by expression selection of random DNA fragments," *Nucleic Acids Research* 20(4):711–717 (Feb. 25, 1992).
Keown et al., "Methods for Introducing DNA into Mammalian Cells," *Methods in Enzymol.* 185:527–536 (1990).
Kerr et al., *Eur. J. Biochem.* 175:65–73 (1988).
Kidd et al., "Dominant negative mutation in galactosyltransferase created by over–expression of a truncated cDNA," *Chemical Abstracts* 111(23):152, abstract 200941n (Dec. 4, 1989).
Kosik et al., "The primary structure and analysis of the squid kinesin heavy chain," *Journal of Biological Chemistry* 265(6):3278–3283 (Feb. 25, 1990).
Kozak and Kabat, "Ping–Pong Amplification of a Retroviral Vector Achieves High–Level Gene Expression: Human Growth Hormone Production," *J. Virol.* 64:3500–3508 (1990).
Lee et al., *J. Bacteriol.* 171:3002–3007 (1989).
Markowitz et al., "Construction and Use of a Safe and Efficient Amphotorpic Packaging Cell Line," *Virology* 167:400–406 (1988).
Miller and Rosman, "Improved Retroviral Vectors for Gene Transfer and Expression," *Biotechniques* 7:980–986 (1989).
Murphy and Efstatiadis, "Cloning vectors for expression of cDNA libraries in mammalian cell," *Proc. Natl. Acad. Sci. USA* 84:8277–8281.
Napoli et al., "Introduction of a chimeric chalcone synthase gene into petunia results in reversible co–suppression of homologous genes in trans," *The Plant Cell* 2(4):279–289 (Apr. 4, 1990).

(List continued on next page.)

Primary Examiner—James Ketter
(74) *Attorney, Agent, or Firm*—McDonnell Boehnen Hulbert & Berghoff

(57) ABSTRACT

Methods for isolating and identifying genetic elements that are capable of inhibiting gene function are disclosed, as well as genetic elements isolated or identified according to the method of the invention and host cells modified by genetic modification using genetic suppressor elements according to the invention.

8 Claims, 5 Drawing Sheets

OTHER PUBLICATIONS

Nomura et al., Selective cloning of ColE1 DNA initiation sequences using the cloning vector M13δE101, *Gene* 18:239–246 (1982).

Ohara et al., "One–sided polymerase chain reaction: The amplification of cDNA," *Proc. Natl. Acad. Sci. USA* 86:5673–5677 (1989).

Patanjali et al., "Construction of a uniform–abundance (normalized) cDNA library," *Proc. Natl. Acad. Sci. USA* 88:1943–1947 (1991).

Patterson et al., "Suicide Selection of Mammalian Cell Mutants," *Methods Exzymol.* 151:121 (1982).

Powell et al., *Proc. Natl. Acad. Sci. USA* 86:6949–6952 (1989).

Ransone et al., *Proc. Natl. Acad. Sci. USA* 87:3806–3810 (1990).

Rimsky et al., *Nature* 341:453–456 (1989).

Rio et al., "A Mammalian Host–Vector System That Regulates Expression and Amplification of Transfected Genes by Temperature Induction," *Science* 227:23–28 (1985).

Robbins et al., "Construction of *E. Coli* expression plasmid libraries: localization of a Psuedorabies virus glycoprotein gene," *J. Mol. Appl. Genet.* 2:485–496 (1984).

Ruther et al., "Exon cloning: Immunoenzymatic identification of exons of the chicken lysozyme gene," *Proc. Natl. Acad. Sci. USA* 79:6852–6855 (1982).

Sarver et al., *Science* 247:1222–1225 (1990).

Sczakiel et al., "Specific inhibition of human immunodeficiency virus type 1 replication by RNA transcribed in sense and antisense orientation from the 5'–leader/gag region," *Biochemical and Biophysical Research Communications* 169(2):643–651 (Jun. 15, 1990).

Takayama et al., "Antisense RNA," *Crit. Rev. Biochem. Mol. Biol.* 25:155–184 (1990).

Trono et al., *Cell* 59:113–120 (1989).

Van der Krol et al., "Modulation of Eukaryotic Gene Expression by Complementary RNA or DNA Sequences," *BioTechniques* 6:958–976 (1988).

Whitaker–Dowling et al., *Virology* 175:358–364 (1990).

```
GTGTCTGGGC GGAGCAAAAT ATGTTCCAAT TGTGTTTTCT TTTGATAGAT TGTGTTTTCT TCTTTCAACA   60
GACAGTCTTT TCTTAGCATC TTCATTTTTC TTTATTTTGT TGACTTGCAT ATTTTCATTT            120
ACAGGCTGCA ATGGTGACAC TTCCATGGTG ACGGTCGTGA AGGG                             164
```

B

```
TGAAAAGATG TATGTCCCAG CTCTCATATT TGGACAGCTC CTAACTTCTA GTAACTATGA            60
TGATGATGAA AAGAAAGTGA CAGGTGGTCG AAATGGCTAT GGAGCCAAAT TGTGTAACAT            120
ATTCAGTACC AAATTTACTG TGGAAACAGC CAGTAGAGAA TACAAGAAAA TGTTCAAACA            180
GACATGGATG GATAATATGG GAAGAGCTGG TGA                                         213
```

C

```
GCCCATTGGT CAGTTTGGTA CCAGGCTACA TGGTGGCAAG GATTCTGCTA GTCCACGATA            60
CATCTTTACA ATGCTCAGCT CTTTGGCTCG ATTGTTATTT CCACCAAAAC ATGATCACAC            120
GTTGAAGTTT TTATATGATG ACAACCAGCG TGTTGAGCCT GAATGGTACA TTCCTATTAT            180
T                                                                            181
```

D

```
TGAATGGTAC ATTCCTATTA TTCCCATGGT GCTGATAAAT GGTGCTGAAG GAATCGGTAC            60
TGGGTGGTCC TGCAAAATCC CCAACTTTGA TGTGCGTGAA ATTGTAAATA ACATCAGGCG            120
TTTGATGGAT GGAGAAGAAC CTTTGCCAAT GCTTCCAAGT TACAAGAACT TCAAGGGTAC            180
```

Fig. 3B

```
TATTGAAGAA CTGGCTCCAA ATCAATATGT GATTAGTGGT GAAG                                         224

E
TGCGTGAAAT TGTAAATAAC ATCAGGCGTT TGATGGATGG AGAAGAACCT TTGCCAATGC          60
TTCCAAGTTA CAAGAACTTC AAGGGTACTA TTGAAGAACT GGCTCCAAAT CAATATGTGA         120
TTAGTGGTGA AGTAGCTATT CTTAATTCTA CAACCATTGA AATCTCAGAG CTTCCCGTCA         180
GAACATGGAC CCAGACATAC AAAGAACAAG TTCTAGAACC CATGTTGAAT GGCACCGAGA         240
AGACACCTCC TCTCATAACA GACTATAGGG AATACCATAC AGATACCACT GTGAAATTTG         300
TTGTGAAGAT GACTGAAGAA AAACTGGCA                                          329

F
CACTCTTTTC AGTTTCCTTT TCGTTGTCAC TCTCTTCATT TTCTTCTTCA TCTGGAACCT          60
TTTGCTGGGC TTCTTTCCAG GCCTTCACAG GATCCGAATC ATATCCCCTC TGAATCAGAA         120
CTTTAATTAA TTCTTTCTTA GGCTTATTTT CAATGATTAT TTTGCCATCT ATTTTCTCAT         180
AGATAAAGCG AGCC                                                          194

G
TCTGCCTCTG CTTTCATTTC TATGGTTATT CGTGGAATGA CTCTTTGACC ACGCGGAGAA          60
GGCAAAACTT CAGCCATTTG TGTTTTTTTC CCCTTGGCCT TCCCCCCTTT CCCAGGAAGT         120
CCGACTTGTT CATCTTGTTT TTCTTGGCT TCAACAGCCT CCAATTCTTC AATAAATGTA         180
```

Fig. 3C

```
GCCAAGTCTT CTTTCCACAA ATCTGA                                              206

GACACGACAC TTTTCTGTGG TTTCAGTTCT TTGTTACTAA GTTTTGGGGA AGTTTTGGTC          60
TTAGGTGGAC TAGCATCTGA TGGGACAAAA TCTTCATCAT CAGTTTTTTC ATCAAAATCT         120
GAGAAATCTT CATCTGAATC CAAATCCATT GTGAATTTTG TTTTTGTTGC TGCTCTCCGT         180
GGCTCTGTTT CTCG                                                           194
                              H

CTGAAACCAC AGAAAAGTGT CGTGTCAGAC CTTGAAGCTG ATGATGTTAA GGGCAGTGTA          60
CCACTGTCTT CAAGCCCTCC TGCTACACAT TCCCAGATG AAACTGAAAT TACAAACCCA         120
GTTCCTAAAA AGAATGTGAC AGTGAAGAAG ACAGCAGCAA AAAGTCAGTC TTCCACCTCC         180
ACTACCGGTG CCAAAAAAAG GGCTGCCCCA AAAGGAACTA AAAGGGATCC AGCTTTGAAT         240
TC                                                                        242
                              I

AATTCAAAGC TGGATCCCTT TTAGTTCCTT TTGGGGCAGC CCTTTTTTTG GCACCGGTAG          60
TGGAGGTGGA AGACTGACTT TTTGCTGCTG TCTTCTTCAC TGTCACATTC TTTTAGGAA         120
CTGGGTTTGT AATTTCAGTT TCATCTGGGA AATGTGTAGC AGGAGGGCTT GAAGACAGTG         180
GTACACTGCC CTTAACATCA TCAGCTTCAA GGTCTGACAC                              220
                              J
```

METHOD AND APPLICATIONS FOR EFFICIENT GENETIC SUPPRESSOR ELEMENTS

This application is a divisional of U.S. Ser. No. 08/039,385, filed Sep. 7, 1993, now U.S. Pat. No. 5,811,234, issued Sep. 22, 1998, which is related as a U.S. National Phase application to PCT/US91/07492, having an International Filing Date of Oct. 11, 1991, which application claims priority under the terms of the Paris Convention and 35 U.S.C. §§120 and 361 to U.S. Ser. No. 07/599,730, filed Oct. 19, 1990, now U.S. Pat. No. 5,217,889, issued Jun. 8, 1993, the disclosures thereof being explicitly incorporated by reference herein.

BACKGROUND OF THE INVENTION

1. Field of the Invention

The invention relates to means for suppressing specific gene function in eukaryotic or prokaryotic cells. More particularly the invention relates to the use of expression of DNA sequences, known as genetic suppressor elements, for the purpose of suppressing specific gene function. The invention provides methods for obtaining such genetic suppressor elements, the genetic suppressor elements themselves, and methods for obtaining living cells which bear a gene suppression phenotype.

2. Summary of the Related Art

Functional inactivation of genes through the expression of specific genetic elements comprising all or a part of the gene to be inactivated is known in the art. At least four mechanisms exist by which expression of such specific genetic elements can result in inactivation of their corresponding gene. These are interference with protein function by polypeptides comprising nonfunctional or partly nonfunctional analogs of the protein to be inhibited or a portion thereof, interference with mRNA translation by complementary anti-sense RNA or DNA, destruction of mRNA by anti-sense RNA coupled with ribozymes, and interference with mRNA by RNA sequences homologous to a portion of the mRNA representing an important regulatory sequence.

Herskowitz, Nature 329: 219–222 (1987), reviews the inactivation of genes by interference at the protein level, which is achieved through the expression of specific genetic elements encoding a polypeptide comprising both intact, functional domains of the wild type protein as well as nonfunctional domains of the same wild type protein. Such peptides are known as dominant negative mutant proteins.

Friedman et al., Nature 335: 452–454 (1988), discloses the use of dominant negative mutants derived from HSV-1 VP16 protein by 3' truncation of the VP16 coding sequence to produce cells resistant to herpes-virus infection. Baltimore, Nature 335: 395–396 (1988), suggests that the method might be applicable as a therapeutic means for treatment of HIV-infected individuals.

Green et al., Cell 58: 215–223 (1989), discloses inhibition of gene expression driven by an HIV LTR, through the use of dominant negative mutants derived from the HIV-1 Tat protein sequence, using chemical peptide synthesis.

Rimsky et al., Nature 341: 453–456 (1989), discloses inhibition of HTLV-1 and HIV-1 gene expression in an artificial plasmid system, using dominant negative mutants derived from the HTLV-1 Rex transactivator protein by oligonucleotide-mediated mutagenesis of the rex gene.

Trono et al., Cell 59: 113–120 (1989), demonstrates inhibition of HIV-1 replication in a cell culture system, using dominant negative mutants derived from the HIV-1 Gag protein by linker insertional and deletional mutagenesis of the gag gene.

Ransone et al., Proc. Natl. Acad. Sci. USA 87: 3806–3810 (1990), discloses suppression of DNA binding by the cellular Fos-Jun protein complex and suppression of Jun-mediated transcriptional transactivation, using dominant negative mutants derived from Fax and Jun proteins by oligonucleotide-directed substitutional or deletional mutagenesis of the fos and jun genes.

Whitaker-Dowling et al., Virology 175: 358–364 (1990), discloses a cold-adapted strain of influenza A virus which interferes with production of wild-type influenza A virus in mixed infections, apparently by a dominant negative mutant protein mechanism.

Lee et al., J. Bacteriol. 171: 3002–3007 (1989), discloses a genetic system for isolation of dominant negative mutations of the beta subunit of E. coli RNA polymerase obtained by hydroxylamine mutagenesis of the rpoB gene.

Chejanovsky et al., J. Virol. 64: 1764–1770 (1990), discloses inhibition of adeno-associated virus (AAV) replication by a dominant negative mutant protein derived from the AAV Rep protein by oligonucleotide-directed substitutional mutagenesis of the rep gene at a position encoding an amino acid known to be critical to Rep protein function.

Suppression of specific gene function by interference at the RNA level, using complementary RNA or DNA sequences, is also known in the art. van der Krol et al., BioTechniques 6: 958–976 (1988), reviews the use of such "antisense" genes or nucleotide sequences in the inhibition of gene function in insect, bird, mammalian, plant, protozoal, amphibian and bacterial cells.

Ch'ng et al., Proc. Natl. Acad. Sci. USA 86: 10006–10010 (1989) discloses that antisense RNA complementary to the 3' coding and non-coding sequences of the creatine kinase gene inhibited in vivo translation of creatine kinase mRNA when expressed from a retrovirus vector, whereas all antisense RNAs complementary to creatine kinase mRNA, but without the last 17 codons or 3' non-coding sequences, were not inhibitory.

Daugherty et al., Gene Anal. Techn. 6: 1–16 (1989) discloses that, for antisense RNA suppression of beta galactosidase (β-gal) gene function in E. coli, best suppression is achieved using plasmids containing a ribosome binding site and expressing short RNA sequences corresponding to the 5' end of the β-gal gene.

Powell et al., Proc. Natl. Acad. Sci. USA 86: 6949–6952 (1989), discloses protection of transgenic plants from tobacco mosaic virus (TMV) when the plants expressed sequences complementary to replicase binding sites, but not when they expressed sequences complementary only to TMV coat protein.

Sarver et al., Science 247: 1222–1225 (1990), discloses the use of antisense RNA-ribozyme conjugates to degrade specific mRNA by complementary RNA binding followed by ribozyme cleavage of the bound mRNA.

Kerr et al., Eur. J. Biochem. 175: 65–73 (1988), reports that even full length antisense RNA is not necessarily sufficient to inhibit gene expression.

Inhibition of gene function can also be accomplished by expressing subregions of RNA which is homologous to, rather than complementary to, important regulatory sequences on the mRNA molecule, and which can likely compete with the mRNA for binding regulatory elements important to expression.

Bunnell et al., Somat. Cell Mol. Genet. 16: 151–162 (1990), discloses inhibition of galactosyltransferase-associated (GTA) protein expression by transcription of an RNA which is homologous to AU-rich elements (AREs) in the 3' untranslated region of the gta gene, which are believed to be important regulatory sequences.

Although gene suppression is quite useful for scientific studies of gene function and holds considerable promise for certain applications in disease therapy and genetic modification of plants and animals, current methods for identifying effective genetic suppressor elements (GSEs) are time consuming and arduous. Interference by dominant negative mutant proteins, for example, either requires extensive knowledge about the functional domain structure of the protein so that reasonably promising candidate mutant proteins can be prepared, or necessitates individual preparation and screening of numerous candidate mutant proteins. Antisense RNA and competitive homologous RNA similarly require extensive individual preparation and screening of candidate inhibitory sequences, absent considerable knowledge about important specific sequences within the RNA. There is, therefore, a need for generalized methods for identifying and isolating GSEs which will allow simplified determination of effective elements without undue experimentation or extensive structure/function knowledge. An ideal method would allow simultaneous analysis of multiple possible candidate GSEs, regardless of their mechanism of action.

BRIEF SUMMARY OF THE INVENTION

The invention relates to the suppression of specific gene function in eukaryotic or prokaryotic cells. More particularly, the invention relates to nucleotide sequences which are capable of suppressing gene function when expressed in a living cell. These nucleotide sequences are known as genetic suppressor elements. Existing methods of suppressing gene function in living cells require considerable information about the structure and function of the gene products, i.e., specific RNA sequences or specific protein domains. Alternatively, existing methods of suppressing gene function can be applied in the absence of detailed structure/function information, but at the expense of the considerable time and effort required to produce many individual mutant proteins or many complementary or homologous RNA or DNA sequences. In contrast, the invention provides a general method for obtaining effective genetic suppressor elements (GSEs) for cloned genes or viruses, without extensive structure/function information, and in a simple selection or screening procedure.

The invention is made possible by two discoveries. First, the inventors have discovered that small peptide fragments, corresponding to only a minute portion of a protein, can inhibit the function of that protein in vivo, even without mutation of the fragments. Second, the inventors have demonstrated that certain random small fragments of DNA, derived from a particular gene or virus, are capable of inhibiting that particular gene or virus in vivo, when they are expressed in a living cell, and that these fragments can be isolated by functional selection for suppression of the gene or virus.

In the method of the invention for obtaining GSEs, randomly fragmented DNA, corresponding to DNA sequences from a gene or virus to be inactivated, is transferred into an expression library capable of expressing the random fragments of DNA in a living cell. Desired living cells are then genetically modified by introducing into them the GSE expression library by standard procedures, and cells containing GSEs are isolated or enriched for by selecting or screening for gene suppression. GSEs are then obtained from the living cells exhibiting the gene suppression phenotype.

GSEs obtained by the method of the invention may be used to genetically modify cells by introducing the GSE into the cell such that it can be expressed and suppress gene function in the genetically modified cell. Alternatively, for some cell types it will be possible to obtain genetically modified cells bearing a gene suppression phenotype as a result of introduction of the GSE library, without ever having to first isolate the GSE.

Genetically modified cells according to the invention can provide benefits, such as virus resistance, which can be commercially important in biotechnology processes using living cells, as well as in food crops derived from virus-resistant cells, or even in agriculturally important transgenic animals. In addition, improved agricultural plants and animals can be produced from genetic modification by suppression of genes responsible for undesirable properties, e.g., cross-pollination of inbred plants. Finally, genetic modification according to the invention may be useful for human therapeutic applications, such as antiviral therapy.

BRIEF DESCRIPTION OF THE DRAWINGS

FIGS. 3 to 3C shows the nucleotide sequence of GSEs derived from human Topoisomerase II, as described in Example 6: A is Seq ID No:1; B is Seq ID No:2; C is Seq ID No:3; D is Seq ID No:4; E is Seq ID No:5; F is Seq ID No:6; G is Seq ID No:7; H is Seq ID No:8; I is Seq ID No:9; J is Seq ID No:10.

DETAILED DESCRIPTION OF THE SPECIFIC EMBODIMENTS

Figure 1:
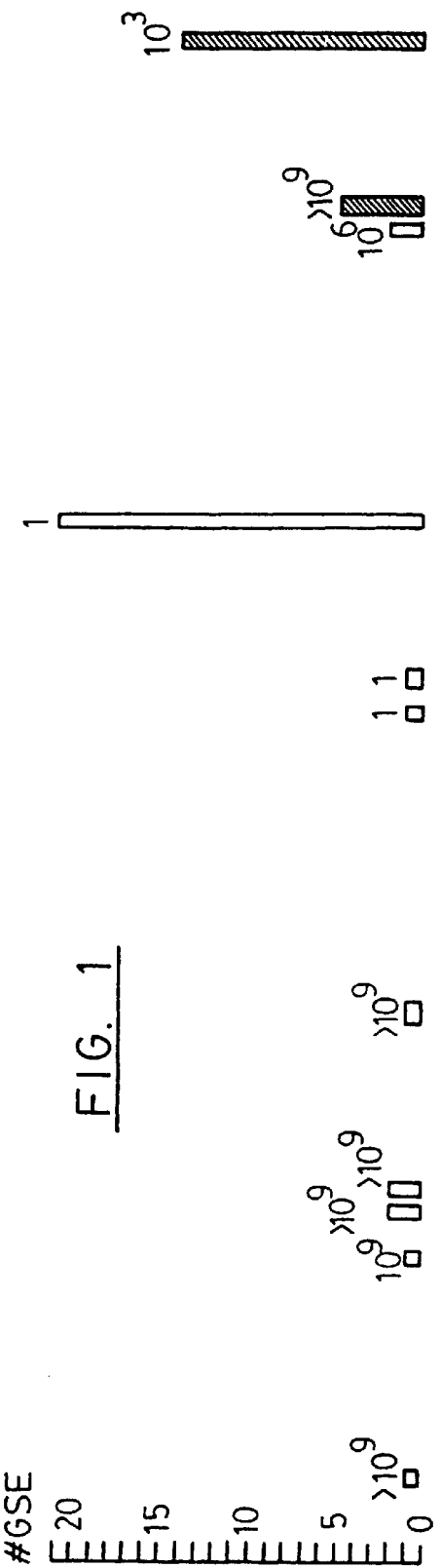
FIG. 1 shows the distribution of GSEs in the lambda genome. Only the genes whose sequences were found in GSEs are indicated in the genetic map of lambda. Open bars indicate sense-oriented GSEs. Hatched bars indicate antisense-oriented GSES. The height of the bars corresponds to the number of sequenced GSE clones for each class. The numbers on top of the bars indicate the extent of suppression of prophage induction by a representative clone of each class.
Figure 1:
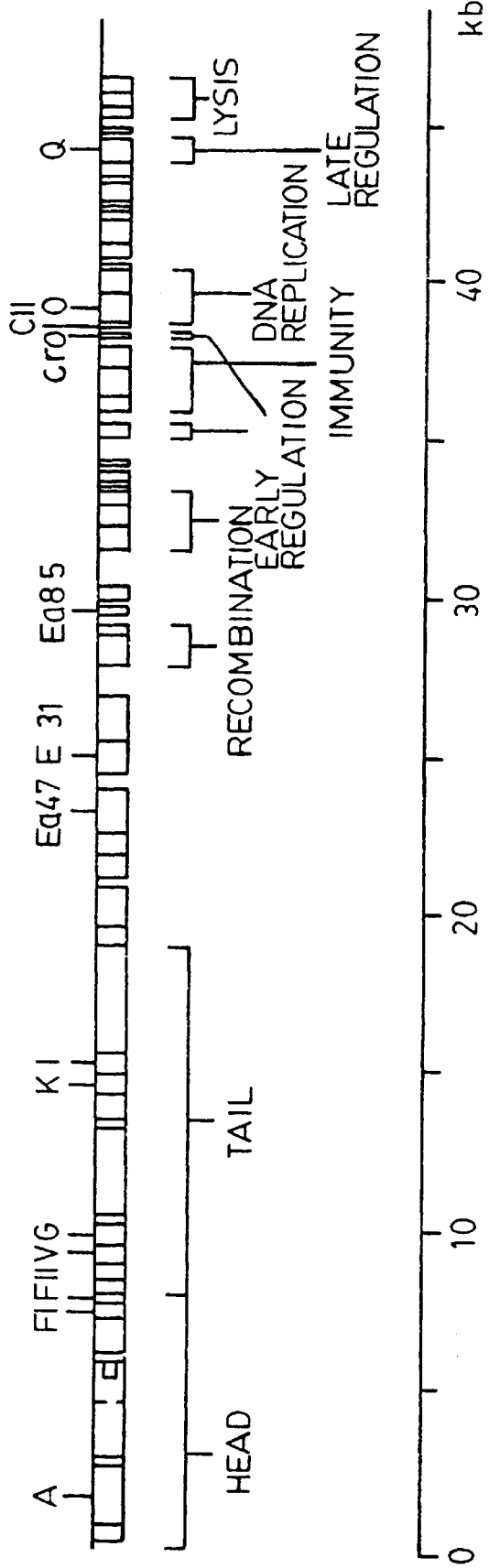

Suppressing the function of specific genes by modifying cells to express gene-specific inhibitory substances is an important approach to various goals in biotechnology and medicine. One of these goals is inhibition of replication of pathogenic viruses in genetically modified cells.

Other suppression targets include, for example, genes associated with tumorigenicity (oncogenes) as well as genes responsible for some undesired properties of agricultural plants or animals. Specific suppression of a target gene requires expression of specially constructed genetic elements that generally include modified DNA sequences derived from the target gene. In one of the currently used approaches to gene suppression, all or a portion of cDNA of the target gene is inserted in a reverse orientation into an expression vector carrying a strong transcription promoter, so that antisense RNA is transcribed. Such antisense RNA can inhibit the function of the target mRNA molecules. Certain genes may also be functionally suppressed by expression of RNA sequences homologous to regulatory sequences in the mRNA. In another, more recent approach, mRNA sequences in an antisense orientation are combined with specific enzymatically active RNA sequences called ribozymes, which are capable of cleaving a target mRNA molecule. Another way to suppress gene expression is to use a mutant form of the target protein that can act in a dominant negative fashion by interfering with the function of the wild-type (normal) form of the same protein.

Although approaches to suppressing genes are thus known in the art, there are no general principles which provide guidance about how to derive DNA elements which can efficiently suppress gene function (genetic suppressor elements, or GSEs) without extensive structure/function information about the RNA or protein, or without undue experimentation. The present invention provides a general method for obtaining GSES. The method of the invention requires only the availability of genomic DNA, total cellular RNA, or of a cloned gene or DNA from a pathogenic virus or intracellularly parasitic microorganism targeted for suppression and the knowledge of a selectable phenotype associated with inactivation of the target gene. This method does not depend on any knowledge of the structure/function organization of the protein encoded by the target gene or the genetic structure of the target virus or microorganism.

In a first aspect, the invention provides a convenient, general method for obtaining GSEs. In this method, purified DNA corresponding to the gene or genome to be suppressed is first randomly fragmented by enzymatic, chemical, or physical procedures. In a preferred embodiment, random fragments of DNA are produced by treating the DNA with a nuclease, such as DNase I. The random DNA fragments are incorporated as inserts in a gene suppression element library, using an expression vector which is capable of expressing the inserted fragments in the cell type in which gene suppression is desired. For general principles of DNase I partial digestion and library construction see *Molecular Cloning, A Laboratory Manual*, Sambrook et al., Eds., Cold Spring Harbor Laboratory, Cold Spring Harbor, N.Y. (1989). In certain embodiments the inserted fragment may be expressed as part of a fusion protein. In other embodiments the inserted fragment alone may be expressed. In another embodiment, ribozyme-encoding sequences may be inserted directly adjacent to the insert to allow for selection of most efficient ribozyme-antisense clones. In still other embodiments the gene suppression element library may be further modified by random mutagenesis procedures known in the art. The inserted fragments may be expressed from either a constitutive or an inducible promoter.

The GSE library is next used to genetically modify living cells of the type in which gene suppression is desired, by introducing the library into the cells by procedures well known in the art, e.g., bacterial or yeast transformation, or transfection of plant or mammalian cells. See, e.g., Keown et al., Methods Enzymol. 185: 527–536 (1990). Of particular interest in mammalian cells is the use of retroviral vectors such as LNCX (Miller and Rosman, Biotechniqes 7:980–986 (1989)); lambda ZD35, Murphy and Efstatiadis, Proc. Natl. Acad. Sci. USA 84: 8277–8281; or derivatives of convenient existing vectors, such as lambda Zap II® (Stratagene, LaJolla, Calif.) that have had inserted sequences that allow retrovirus gene expression. The genetically modified cells containing effective GSEs can be screened for or selected in a variety of ways. For example, when the suppression is directed against a cytolytic virus, cells containing effective GSEs may be selected on the basis of cell survival upon virus infection and development of cytopathic effect. In another embodiment, suppression is directed against a non-cytolytic virus or against a gene encoding a cell surface antigen. In this embodiment, selection is against the presence of the viral or cell surface antigens. This is accomplished by reacting the genetically modified cells with specific primary antibodies against the viral or cell surface antigens. "Unsuppressed" cells may then be eliminated by the addition of complement, or may be separated from "suppressed" cells by addition of fluorescent secondary antibody against the primary antibody, followed by fluorescence-activated cell sorting. For a general description of immunological selection and screening techniques see Davis et al., *Microbiology*, Harper and Row, Philadelphia, Pa. (1980). In another embodiment, suppression is directed against genes that must be expressed in order for cells to grow under specific procedures. In this embodiment, cells containing effective GSEs can be selected by "suicide selection" procedures that select for cells which cannot grow in the selective medium. See Patterson et al., Methods Enzymol. 151: 121 (1982).

In yet another embodiment, suppression is directed against growth-suppressing genes, such as tumor suppressors. In this embodiment, cells containing effective GSEs may be screened on the basis of morphological transformation of cell colonies.

The GSE is finally obtained from the selected cells by procedures known in the art. In one embodiment, the GSE is isolated by use of the polymerase chain reaction with DNA obtained from the selected cells and with primers homologous to sites on the vector flanking the insert. In another embodiment, the GSE expression library may be prepared in shuttle vectors, allowing efficient recovery of shuttle vectors containing GSEs (See, e.g., Groger et al., Gene 81: 285–294 (1989); Rio et al., Science 227: 23–28 (1985) for examples of shuttle vectors). Of course, in bacteria simple plasmid isolation procedures can be employed directly on the bacterial clone expressing the genetically suppressed phenotype. Finally, GSEs can be isolated by standard cloning techniques well known in the art using vector specific probes although this might be more laborious than other embodiments herein described.

In a second aspect, the invention provides GSEs which are most likely more effective than existing GSEs, since GSEs obtained according to the method of the invention may be selected from a very large number of possible DNA sequences, whereas existing GSEs have been the result of trial and error analysis of only a few designs. GSEs obtained according to the methods of the invention may operate according to principles different from those behind existing gene suppression methods, since it is the gene suppression phenotype, and not the mechanism, which is selected. GSEs obtained according to the methods of the invention are useful for the genetic modification of living cells for scientific studies, for biotechnology processes, for agricultural purposes and for human and animal therapeutic purposes. In addition, oligonucleotide or oligopeptide GSEs can be readily prepared which correspond to the nucleotide or amino acid sequence of the GSE obtained according to the method of the invention. These oligonucleotides, which may be standard oligonucleotides, standard oligodeoxynucleotides or chemically modified derivatives of oligonucleotides or oligodeoxynucleotides, will be capable of inhibiting specific gene function, by virtue of homology to the identified GSE. Such oligonucleotide inhibitors will be particularly useful for pharmaceutical purposes.

In a third aspect, the invention provides genetically modified living cells that contain effective GSEs, whereby in such cells particular genes are suppressed by the expression of the GSEs. In a preferred embodiment, such genetically modified cells are produced by introducing into the cell, by standard procedures, an expression vector containing a specific GSE obtained by the method of the invention and capable of expressing the GSE in the cell. In another embodiment the genetically modified cell is obtained directly from selection of cells into which the GSE library has been introduced, without any previous isolation of the GSE contained in the genetically modified cell.

In a fourth aspect, the invention provides a convenient method for discovering GSE, associated with a particular phenotype, rather than with a particular known gene. In this aspect, the method provides GSEs corresponding to recessive genes that, when inactivated, confer a selectable or screenable phenotype upon a cell having such inactive genes. This method uses a random fragment expression system as previously described. However, the starting material is different. GSEs in this case are isolated from random fragment expression libraries prepared from either genomic DNA or total cellular cDNA. When used to obtain bacterial or lower eukaryotic GSEs, genomic DNA is preferred, for reasons of convenience. In contrast, cDNA is preferred for GSEs from higher eukaryotes, due to its lower complexity.

In a fifth aspect, the invention provides synthetic peptides and oligonucleotides that are capable of inhibiting the function of particular gene products. Synthetic peptides according to the invention have amino acid sequences that correspond to amino acid sequences encoded by GSEs according to the invention. Synthetic oligonucleotides according to the invention have nucleotide sequences corresponding to the nucleotide sequences of GSEs according to the invention. Once a GSE is discovered and sequenced, and its orientation is determined, it is straightforward to prepare an oligonucleotide corresponding to the sequence of the GSE (for antisense-oriented GSES) or to prepare a peptide corresponding to an amino acid sequence encoded by the GSE (for sense-oriented GSEs). In certain embodiments, such synthetic peptides or oligonucleotides may have the complete sequence encoded by the GSE or present in the GSE, respectively. In certain other embodiments, the peptide or oligonucleotide may have only a portion of the GSE-encoded or GSE sequence. In such latter embodiments, undue experimentation is avoided by the observation that many independent GSE clones corresponding to a particular gene will have the same 5' or 3' terminus, but generally not both. This suggests that many GSEs have one critical endpoint, from which a simple walking experiment will determine the minimum size of peptide or oligonucleotide necessary to inhibit gene function. For peptides, functional domains as small as 6–8 amino acids have been identified for immunoglobulin binding regions. For antisense oligonucleotides, inhibition of gene function can be mediated by oligonucleotides having sufficient length to hybridize to their corresponding mRNA under physiological conditions. Generally, oligonucleotides having about 12 or more bases will fit this description. Those skilled in the art will recognize that peptide mimetics and modified oligonucleotides are equivalent to the peptides and oligonucleotides according to the invention, since both can be prepared according to standard procedures once the sequence necessary for inhibition is known.

The following examples are provided as means for illustration and are not limiting in nature.

EXAMPLE 1

Suppression of Gene Function by Expression of a DNA Sequence Encoding a Small Polypeptide P-glycoprotein, the product of the human mdr1 gene, is a multidrug transporter that renders mammalian cells resistant to various lipophilic drugs by pumping these drugs out of cells. See Chen et al., Cell 47: 381 (1986). A short segment of mdr1 cDNA, corresponding to exon 7 of the mdr1 gene and encoding a 57 amino-acid long peptide, was inserted by standard procedures into an expression vector (pneoMLV), containing a G418-resistance gene, neo, as a selectable marker. One of the constructs (construct 1) was made in such a way that the mdr1-derived sequence was preceded by the translation initiation codon at the 5' end. At the 3' end, this sequence was adjoined to an open reading frame present in the vector sequence, so that the mdr1-derived sequence formed the N-terminal portion of the resulting fusion peptide. In another construct (construct 2), the mdr1-derived sequence was preceded by the initiation codon and followed by a stop codon, giving rise to an entirely mdr1-derived 58 amino acid protein (including the initiating methionine). Constructs 1 and 2, as well as a control pSV2neo plasmid, were transfected into human KB-8-5 cells, which display a moderate amount of multidrug resistance due to mdr1 expression. Transfectants were selected with G418, and possible changes in P-glycoprotein function were tested by determining the levels of resistance of individual transfectants to the cytotoxic drugs vinblastine and colchicine.

All ten of the control transfectants obtained with pSV2neo had the same levels of drug resistance as the recipient KB-8-5 cell line. In contrast, twelve of fifteen transfectants obtained with construct 1 had significantly decreased levels of drug resistance (in some cases less than one-half the resistance of KB-8-5). Five of eight transfectants obtained with construct 2 also showed a significant decrease in drug resistance relative to control KB-8-5 cells. These results indicate that a short segment of P-glycoprotein, comprising only 4.5% of the protein length, can serve as a genetic suppressor element for P-glycoprotein function. There is no specific function presently associated with this segment of P-glycoprotein, although this segment includes the amino acid residue 185 known to be a determinant of the specificity of P-glycoprotein-drug interactions.

These results demonstrate that short protein fragments without a known function can serve as dominant negative inhibitors of the wild-type protein, suggesting that dominant negative inhibitors may be selected from a library expressing random short fragments of the target protein.

EXAMPLE 2

Preparation of an Antiviral Genetic Suppressor Element Library

Lambda phage DNA was fragmented by partial digestion with DNaseI in the presence of $Mn^{++}$ ions and NcoI linkers were added to the termini of the resulting fragments by blunt-end ligation after filling in the termini with T4 DNA polymerase and Klenow fragment of DNA polymerase I. Fragments of 350–450 bp size were then isolated after NcoI digestion and agarose gel electrophoresis. The fragment mixture was inserted into a plasmid expression vector pKK233-2, which carries a gene for ampicillin resistance and expresses inserted sequences using an IPTG-inducible trc promoter and a specific translation initiation region. See Amann et al., Gene 40: 183 (1985). The vector was modified to provide for appropriate termination of translation of the inserted segment by insertion of the DNA sequence 5' CATGGTGACTGACTGAAGCT 3' into the NcoI and HindIII sites of the polylinker. The ligated mixture was used to transform E. coli strain PLK-F' (sensitive to lambda), and a library of approximately 80,000 ampicillin-resistant clones was obtained.

EXAMPLE 3

Identification and Isolation of Genetic Suppressor Elements

To identify and isolate genetic suppressor elements in a library prepared as described in Example 2, the amplified library was tested for the presence of clones resistant to infection by bacteriophage lambda. A library comprising cells transformed with an insert-free pKK233-2 vector was used as a control. After IPTG induction, aliquots of $10^6$ cells from the amplified library and the control were infected with lambda phage and plated on ampicillin-containing plates. The multiplicity of infection was selected so as to allow for the survival of 1%–3% of the infected control bacteria. After the first infection, there was no major difference in the number of surviving cells between the library and the control cells. Plasmid DNA was then extracted from the mixture of approximately $3\times10^4$ library-derived colonies that survived phage infection, and this DNA was used to transform plasmid-free bacteria. The new library was also infected with lambda, and this time approximately 10% of the cells in the library were found to be resistant under the conditions of infection that allowed either 3% or 0.02% of the control cells to survive. Plasmids were then isolated from 30 surviving colonies and used individually to transform fresh E. coli cells. After infection with lambda, cells transformed with 28 of 30 selected plasmids showed resistance to lysis.

Parallel studies with the control plasmid showed no increase in the number of resistant colonies after three rounds of selection, indicating that the immunizing clones were specific to the lambda fragment library. Restriction enzyme analysis showed that almost all the plasmids carried NcoI inserts of the expected size (350–450 bp). Based on the observed frequency of the resistant cells, approximately 0.3% of the clones in the original fragment library carried GSEs. Only a minority of the suppressing and infected bacterial colonies showed chromosomal integration of lambda sequences after infection, thus indicating that induction of lysogeny is not a major mechanism for protection by the suppressing clones.

Another library was prepared as described in Example 2, except that the insert fragments were of an average size of 600–700 bp. Although this library also contained suppressing clones, their frequency was an order of magnitude lower than in the 350–450 bp library.

These results demonstrate that random fragmentation of DNA homologous to a gene whose function is to be suppressed, followed by library construction and biological selection or screening, is a feasible general approach for the isolation of genetic suppressor elements.

EXAMPLE 4

Characterization of Genetic Suppressor Elements

Fifty-one of the isolated GSE clones were characterized by DNA sequencing. The sequenced GSEs fell into 11 classes, each class representing a different region of the lambda genome. See FIG. 1. The suppression efficiency of different classes of GSE was evaluated by the following tests. (a) Plating efficiency of transformed bacteria was measured after lambda infection at high m.o.i. Bacteria transformed with any of the GSE showed either none or a minor (<2-fold) decrease in the plating efficiency. (b) The phage titer was determined by plaque assay using the amounts of phage that produced $10^9$ plaques in control bacteria. No plaques were discernible with most types of GSE, though some GSE allowed for the formation of phage plaques at the incidence of $10^{-5}$ to $10^{-7}$, apparently reflecting the appearance of GSE-insensitive mutant phage. (c) To determine the effect of GSEs on prophage induction, representative clones of each class were introduced into a lysogenic strain of E. coli and the phage titer was determined after induction. Eight classes of GSE decreased the titer of the induced phage by three or more orders of magnitude, but GSEs of the other three classes had no effect on prophage induction.

Sense-oriented GSEs

Eight classes of GSE contained lambda gene fragments inserted in the sense orientation relative to the promoter. The inserted fragments encoded either partial or complete lambda proteins. Translation was initiated from the native initiation codon, from a linker-derived initiation codon that was in-frame with the coding sequence, or from an initiation codon within the fragment. Two or more identical copies were found for eight different GSEs. The most abundant class of GSE contained sequences of the gene Ea8.5, previously of unknown function. This class of GSE is described in Example 5.

Two sense-oriented classes of GSE, each represented by a single clone, contained truncated sequences from lambda genes having unknown functions. The first of these encoded the C-terminal 216 of 296 amino acids encoded by the full-length Ea31 gene. The second GSE encoded the C-terminal 88 of 410 amino acids encoded by the full-length Ea47 gene. The coding sequence of each GSE was in frame with a translation initiation codon from the linker. These GSEs inhibited infection of transformed bacteria by lambda phage, but did not suppress lysogen induction.

Another GSE class, represented by 2 clones, contained an intact cro gene in sense orientation. Since cro encodes a regulatory protein that suppresses expression of lambda early genes, its GSE effect was expected.

Four classes of GSE encoded truncated forms of phage particle structural proteins. One such GSE encoded the C-terminal 80 of 117 amino acids encoded by the full-length FI gene, as well as the N-terminal 40 amino of 117 amino acids encoded by the full-length FII gene. The FI and FII genes encode lambda head proteins. Another GSE-encoded the C-terminal 159 of 198 amino acids encoded by the FII-length K gene, as well as the N-terminal 121 of 223 amino acids encoded by the full-length I gene. The K and I genes encode lambda tail proteins.

Two other GSE classes encoded truncated forms of tail proteins V or G. The two clones of the first class encoded identical amino acid sequences (the first 145 of 256 amino acids of V protein), as did the two clones of the second class (the first 113 of 140 amino acids of G protein). In neither case, however, could the two clones be siblings, since their nucleotide sequences were non-identical. To confirm the protein interference mechanism of action, the V protein GSE was mutated to introduce a nonsense mutation in the fourth codon. Introduction of this mutation abolished GSE activity.

Antisense-oriented GSEs

Three classes of GSE contained lambda gene sequences inserted in antisense orientation relative to the promoter. One such clone contained an internal segment of lambda gene A (positions 1050–1470), which is involved in DNA packaging. Two other classes of antisense GSEs were represented by multiple clones. The first class included 12 non-identical clones encoding RNA complementary to the 5' portion of lambda gene Q, which positively regulates lambda late transcription. All GSEs in this class overlapped the naturally-occurring lambda antisense transcript $P_{aQ}$, which downregulates Q expression. None of these GSEs initiated more than 70 bp upstream from the normal $P_{aQ}$ promoter, although they contained downstream flanking sequences of variable lengths. Seven of these GSEs initiated within a 16 bp region.

Figure 2:
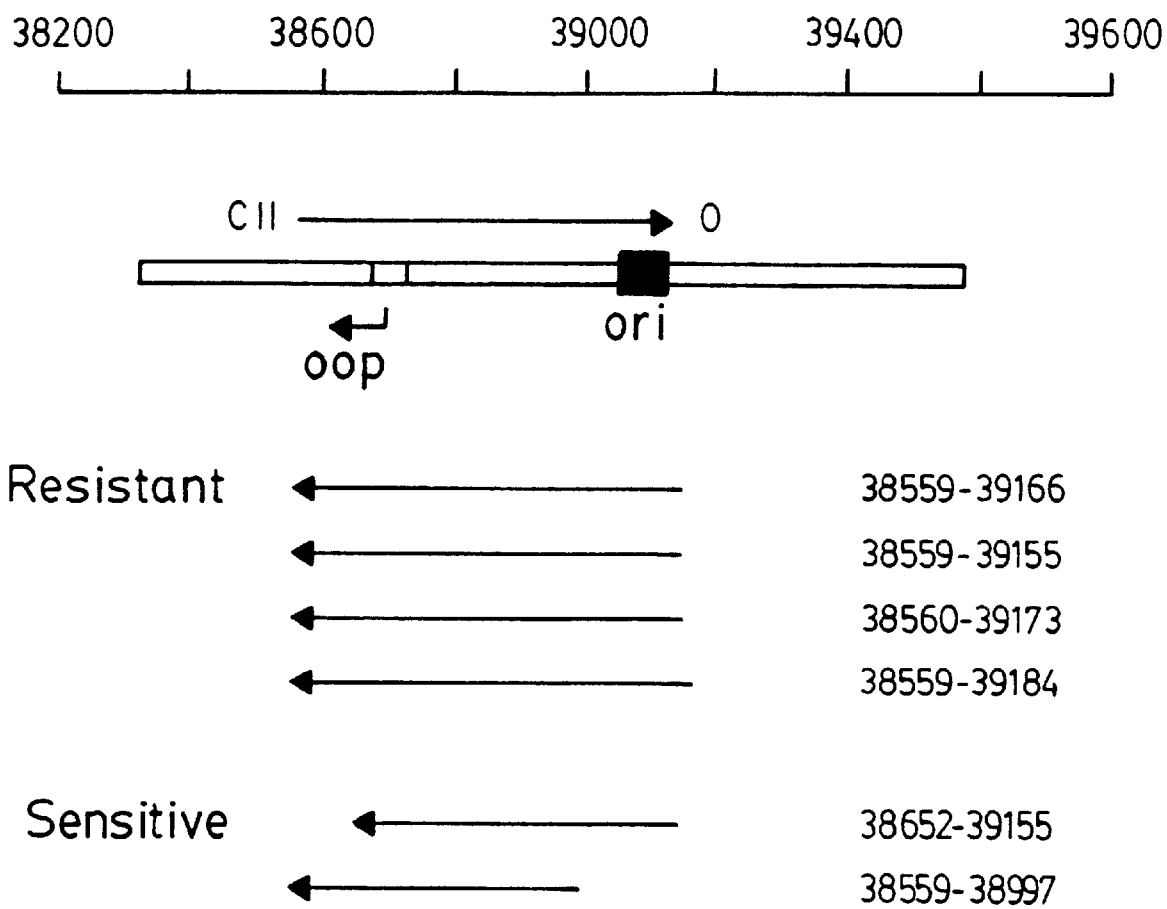
FIG. 2 shows the distribution of the oop/ori class of GSEs and the corresponding lambda resistance phenotypes. Arrows indicate the direction of transcription. The map position of the antisense oop transcript is according to Krinke and Wulff, Genes Dev. 1: 1005 (1988). The four top clones were obtained by GSE selection. The two bottom clones were constructed by PCR synthesis using the corresponding primers.

Another class of antisense GSEs included four different GSEs that encoded nearly identical antisense RNA sequences corresponding to the 3' end of the lambda gene CII, which regulates lysogeny, and the 5' half of lambda gene O, which encodes a lambda replication protein. As shown in FIG. 2, each of these GSEs included the lambda origin of replication, located in the middle of lambda gene O, as well as the naturally-occurring lambda antisense transcript oop, which is complementary to CII and normally suppresses CII. While these GSEs suppress lytic infection, overexpression of oop normally enhances lambda lytic infection. Two truncated variants of these GSEs were prepared to determine whether some portion of the GSEs other than the oop sequences was responsible for the observed suppression. One variant lacked a 93 bp segment encoding most of the oop sequence, but retained the 5' portion of lambda gene O, including the lambda origin of replication. The other variant lacked a 158 bp segment of lambda gene O, comprising the lambda origin of replication, but retained the oop sequence and the remainder of the 5' of lambda gene O. Neither variant suppressed lambda infection, indicating that both the oop and gene O sequences, including the lambda origin of replication, were required for suppression.

Interpretation of Results

The GSEs characterized in these studies act by a variety of mechanisms. First, numerous GSEs encoded truncated versions of lambda structural proteins, and thus apparently act as dominant negative mutants, interfering with phage particle assembly. Second, some GSEs encode antisense RNAs that are complementary to required lambda gene transcripts. Since these GSEs contained naturally-occurring regulatory antisense transcripts of lambda, this demonstrates that random fragment selection of GSEs can be used to identify natural mechanisms of gene suppression. This is confirmed by a third type of GSE, which encodes intact regulatory proteins of lambda. Fourth, some GSEs encode antisense RNAs that act by a suppression mechanism that is distinct from the traditional antisense RNA mechanism of simple interference with structural gene function. These GSEs encoding the oop/O gene antisense RNAs likely interfere with DNA replication directly, since they coincide with the lambda origin of replication. Such interference may result from interference with RNA annealing that might be involved in initiation of lambda DNA replication.

Both sense-oriented and anti-sense oriented GSEs have shown coincidence or near coincidence of termini among different clones, indicating strict sequence limitations for GSEs. This finding indicates that the random fragment selection strategy provided by the invention is critical for successfully obtaining GSEs. In addition, random fragment selection for GSEs that are larger or smaller than the 300–500 bp fragments used in these studies can reveal additional classes of GSEs. Selection of very short GSEs that can be used to identify antisense oligonucleotide or peptide sequences that can be synthesized chemically to produce bioactive molecules is of particular interest.

EXAMPLE 5

Use of Random Fragment Selection of GSEs to Identify Novel Gene Function

In the characterization studies described in Example 4, the most abundant class of GSE contained sequences of the lambda gene Ea8.5 inserted in sense orientation. The function of the Ea8.5 gene has been previously unknown. It is transcribed in the delayed early stage of lytic infection, but is not required for either lytic or lysogenic infection. The gene encodes a 93 amino acid protein. Some of the GSEs encoded intact Ea8.5 protein, while others encoded truncated proteins, missing 7 to 38 C-terminal or 3 to 10 N-terminal amino acids. The suppression effect was abolished by introduction of a frameshift mutation into the second codon, indicating that Ea8.5 protein itself, in intact or truncated form, was required for suppression. Expression of Ea8.5 in a lysogenic strain did not suppress prophage induction, indicating that Ea8.5 acts at an initial stage of infection, such as phage entry into the host cell. Bacteria expressing Ea8.5 were deficient in maltose metabolism, as assayed on McConkey media with maltose, but were proficient in galactose, lactose, mannose and arabinose metabolism. The malK-lamB RNA, from one of the three maltose operons of $E.$ $coli$, was absent in bacteria expressing Ea8.5 protein, indicating that suppression is associated with inhibition of the maltose operon encoding the lamB lambda receptor. GSEs encoding truncated Ea8.5 protein showed an incomplete but still significant suppression of malK-lamB RNA production and maltose metabolism. We have also tested Ea8.5-transformed bacteria for resistance to imm$^\lambda$h$^{80}$ a recombinant of phages lambda and $\phi$80 that enters the cell through a receptor different from LamB. The transformants were found to be sensitive to this phage, thus confirming the receptor-mediated mechanism of protection by Ea8.5 GSEs. These results indicate that random fragment selection of GSEs can be used to identify a previously unknown gene function.

EXAMPLE 6

Development of GSEs for Human Topoisomerase II

Topoisomerase II is a DNA unwinding enzyme that serves as a target for many anti-cancer drugs, including etoposide, doxorubicin and amsacrine. The enzyme normally acts by double-strand DNA cleavage, followed by strand passage and religation of the breaks. Anti-cancer drugs cause trapping of the enzyme in complexes having double-strand breaks held together by the enzyme, thereby leading to lethal damage in replicating cells. Some cell lines that are resistant to anti-cancer drugs that interact with topoisomerase II have decreased expression of this enzyme.

Random fragment selection of GSEs requires transfer of the expression library into a very large number of recipient cells. Therefore, to prepare a random fragment library containing GSEs for topoisomerase II, the efficient retroviral vector system was chosen. Overlapping cDNA clones spanning the entire coding sequence for topoisomerase II were mixed and randomly fragmented into 250–350 bp fragments by DNase, as described in Example 2. After ligation with a synthetic adaptor providing translation initiation and termination codons, the fragment mixture was amplified by PCR, using adaptor-derived primers. The amplified mixture was cloned into the LNCX retroviral vector which contains a neo gene. Miller and Rosman, Biotechniqes 7:980–986 (1989). A fragment library containing 20,000 independent clones was obtained, and was used to transfect amphotropic and ecotropic virus-packaging cell lines derived from NIH 3T3 cells, to effect ping-pong replication-mediated amplification of the virus. See Kozak and Kabat, J. Virol. 64: 3500–3508 (1990). This resulted in a random fragment expression library (RFEL), a set of recombinant retroviruses containing a representative mixture of inserts derived from topoisomerase II gene sequences.

The uniformity of sequence representation in RFEL was monitored as follows. NIH 3T3 cells were infected with virus-containing supernatant, followed 24 hours later by PCR amplification of integrated proviral insert sequences in the presence of [$^{32}$P] alpha-dNTP. An aliquot of the PCR-amplified mixture was subjected to gel electrophoresis to establish the absence of predominant bands. Another aliquot was used as a probe for a Southern blot of topoisomerase II cDNA digested with several frequently cutting restriction enzymes. A representative sequence mixture was obtained, as evidenced by the absence of a predominant band in the first test, and uniform hybridization to all fragments in the second test.

RFEL was then used to infect HeLa cells, and the infectants were selected with G418. Colonies of G418-resistant cells, having about 50–70 cells each, were then exposed to etoposide at a concentration of 200 ng/ml. Approximately 50 of 10,000 G418-resistant colonies were etoposide resistant, compared to a frequency of <$10^{-4}$ when insertless retroviruses were used as a control. Cell lines were isolated from etoposide-resistant colonies. Amphotropic and ecotropic packaging cell lines producing RFEL were also selected for etoposide resistance. Virus from etoposide resistant packaging cell lines was used to infect HeLa cells, which were then selected with G418. G418-resistant infectants were challenged with three topoisomerase II-interactive anticancer drugs: etoposide, teniposide and amsacrine. A high proportion of infected cells were resistant to all three drugs, thus demonstrating that etoposide selection of mouse packaging cell lines has led to the generation of GSEs active in both human and mouse cells. These infectants were also used to establish cell lines. RFEL-derived inserts were recovered from etoposide resistant cell lines by PCR and recloned into LNCX vector. The newly-derived clones were then individually tested for the ability to confer resistance to etoposide upon transfection into HeLa cells, to confirm the GSE activity of the corresponding inserts.

Sequence analysis of 26 different isolated clones revealed that 16 of them were inserted in antisense and 10 in sense orientation. Of the 10 GSEs confirmed so far, 5 were sense and 5 antisense, as shown in Table 1. The sequences of the confirmed GSEs are shown in FIGS. 3A–3C. The sense-oriented inserts of the confirmed GSEs encode 37–99 amino acid long topo II-derived peptides, initiating either from the ATG codon provided by the adaptor, or from an internal ATG codon within the open reading frame of Topoisomerase II, located close to the 5′ end of the insert in an appropriate context for translation initiation. Four of the confirmed antisense GSEs come from the 3′ third of the cDNA and one from the 5′ end of cDNA, including the translation start site. Of the confirmed sense-oriented GSEs, three are derived from the central portion of the protein that includes the active site tyrosine-804 that covalently binds to DNA and the "leucine zipper" region involved in dimerization of Topoisomerase II. One GSE peptide is derived from the region near the N-terminus and another from the region near the C-terminus of the protein; no known functional sites are associated with either segment.

These results establish that the principles for producing GSEs in a prokaryotic system (lambda phage in *E. coli*) can be extended to a mammalian or human system through the use of an amphotropic retroviral vector system. As in the prokaryotic system, the GSEs obtained act according to multiple mechanisms. In addition, these results show that GSEs produced from one mammalian species can be active in another mammalian species. Finally, these results demonstrate that GSEs for topoisomerase II are obtainable using a random fragment expression library. Such GSEs are useful for positive selection of genetically modified mammalian cells, in vitro, and for human gene therapy for rendering bone marrow resistant to anticancer drugs that interact with Topoisomerase II.

TABLE 1

CONFIRMED TOPOISOMERASE II-DERIVED GSE

| Clones | Orientation (Sense/ Antisense) | Position in cDNA[a] | Position of peptide[b] |
|---|---|---|---|
| 2V | Antisense | −18–145 | |
| Σ11 | Sense | 393–605 | 134–201 |
| 6 | Sense | 2352–2532 | 808–844 |
| 5 | Sense | 2511–2734 | 846–911 |
| Σ28 | Sense | 2603–2931 | 879–977 |
| Σ2 | Antisense | 3150–3343 | |
| Σ20 | Antisense | 3486–3692 | |
| 39 | Antisense | 3935–4127 | |
| 12S, ΣVP | Sense | 4102–4343 | 1368–1447 |
| Σ8 | Antisense | 4123–4342 | |

[a]Position in the cDNA sequence of topoisomerase II; residues numbered as in Tsai-Pflugfelder et al., Proc. Natl. Acad. Sci. USA 85: 7177–7181 (1988).
[b]Position of the peptide encoded by sense-oriented GSEs in the amino acid sequence of topoisomerase II; translation assumed to initiate from the first ATG codon in the correct open reading frame.

EXAMPLE 7

Preparation of GSEs that Abolish HLA Antigen Expression

Destruction of target cells by cytotoxic T lymphocytes requires the presence of major histocompatibility (MHC, HLA) Class I antigens on the target cells for adhesion as well as for triggering of the antigen-specific T cell response. Masking of MHC Class I antigens prevents xenograft rejection of human donor cells in mouse recipients. Thus, target cells can be protected from immune destruction by deliberate reduction of MHC Class I antigens on the surface of such cells. Target cells resistant to destruction by cytotoxic T lymphocytes are useful for a variety of purposes. For example, they can be used as human tumor xenografts that can act as in vivo models for anticancer drug testing in immunocompetent mice. Moreover, some such human tissue culture cells e.g., pancreatic cells can be used for tissue transplantation into unmatched recipient patients.

Expression of MHC Class I antigen on the cell surface requires co-expression of $\beta_2$-microglobulin, a highly conserved protein. Thus, both $\beta_2$-microglobulin and MHC Class I protein are targets for suppression that leads to resistance to immune destruction. Mice that are deficient in $\beta_2$-microglobulin production express little if any MHC Class I antigen on cell surfaces, yet are fertile and apparently healthy, except for the absence of CD4⁻8⁺ T cells.

Tissue culture cells that are resistant to immune destruction are prepared by infection with a random fragment expression library for GSEs derived from $\beta_2$-microglobulin. The nucleotide sequence for human $\beta_2$-microglobulin was described by Gussow et al., J. Immunol. 139: 3132–3138 (1987). The complete human $\beta_2$-microglobulin cDNA sequence is used to prepare RFEL, as described in Example 6, and infected cells are selected for G418 resistance. Infected cells are then selected for resistance to immune destruction by injection into immunocompetent mice. The selected cells are used to isolate the GSEs, as described in Example 6. The isolated GSEs are then used to render other cell types resistant to immune destruction. Alternatively, the GSE library is prepared from cDNA of all MHC Class I genes.

EXAMPLE 8

Preparation of a Normalized Random Fragment Library for Total Human cDNA

It is desirable to be able to obtain GSEs for any gene, the suppression of which will have a desirable effect, without requiring special knowledge of the gene structure or function. Examples of such genes include presently unknown tumor suppressor genes or genes that potentiate the cytotoxic action of anticancer drugs.

For isolation of GSEs corresponding to a mammalian gene that is expressed at moderate or high levels, an RFEL of total cDNA can be used. However, for isolation of GSEs corresponding to genes that are expressed at low levels, the use of normalized cDNA libraries is desirable. Preparation of a normalized cDNA population has been described by Patanjali et al., Proc. Natl. Acad. Sci. USA 88:1943–1947 (1991). Poly(A)+ RNA is extracted from HeLa cells and randomly primed short fragment cDNA is prepared. For purposes of preparing random fragment libraries the procedure is modified by ligating the cDNA to a synthetic adaptor providing translation initiation and termination codons, followed by PCR amplification, as described in Example 6. PCRs are carried out in many separate reactions that are subsequently combined, in order to minimize random over- or underamplification of specific sequences and to increase the yield of the product. The PCR amplified mixture is then size-fractionated by gel electrophoresis and 300–500 bp fragments are taken.

The representation of different mRNA sequences is monitored by Southern blot hybridization of the mixture, using a series of six to eight probes corresponding to mRNAs of different abundance. Ribosomal DNA and $\beta$-actin are good high abundance probes, while c-myc and dhfr serve as moderate abundance probes and C-H-ras and c-K-ras are low abundance probes. Normalization is accomplished by denaturation and reannealing of the PCR-amplified cDNA, using 24, 48, 72, 96 and 120 hour time points for reannealing. Single and double stranded DNAs are then separated from each reannealed mixture by hydroxyapatite chromatography. Single stranded DNA fractions from each time point are PCR-amplified using adaptor derived primers and are analyzed by Southern hybridization for relative abundance of different sequences. Selective under-representation of the most abundant species may be avoided by mixing two library aliquots reannealed at different times at a ratio calculated to give the most uniform representation.

The normalized cDNA population is then cloned into the LNCX retroviral vector, as described in Example 6. The library is then amplified by ping-pong amplification, using a 1:1 mixture of ecotropic packaging cell line GP+E86 and amphotropic packaging cell line GP+envAm12, Markowitz et al., Virology 167: 400–406 (1988), in 10–15 separate batches to produce approximately 106 independent clones per batch. We have obtained a yield of amphotropic virus 11–12 days after infection of >$10^6$ per 10 ml media supernatant from a single 100 mm plate. These amphotropic virus have fairly even representation of different fragments, but at later stages individual virus-producing clones begin to predominate, thereby making sequence representation uneven. Uniform sequence representation is monitored by rapid extraction of DNA from cells infected with packaging cell supernatant, followed by linker-specific PCR amplification and Southern hybridization with different probes.

EXAMPLE 9

Use of Normalized Random Fragment GSE Libraries to Identify Recessive Genes

In order to obtain GSEs for any particular gene from a library representing total mRNA, it is necessary to be able to generate a very large library. Somatic tissues of higher eukaryotes express mRNA for about 10,000 genes. For an average mRNA length of about 2.5 kb, the total mRNA or cDNA complexity for a given tissue type is about 25,000 kb. We have discovered that in a library prepared from a 6 kb cDNA encoding human topoisomerase II, approximately 1 in 200 clones carried GSEs. This corresponds to a frequency of about one GSE for every 33 clones for every kilobase of library complexity. Thus, for a library of 25,000 kb complexity, the frequency of GSEs for a particular gene is about 1 in 825,000 clones, or approximately $10^{-6}$.

To be certain that at least one GSE is present for every gene, a library of about $10^7$ independent clones is prepared, as described in Example 7. Some twenty 150 mm plates, each having about 50,000 colonies, is sufficient for screening of about $10^6$ infected HeLa cells. Thus, 10–15 batches of such twenty plate selections are sufficient for isolation of a GSE for any desired recessive gene for which a negative selection is possible (e.g., 200 ng/ml etoposide for topoisomerase II GSES). As in Example 6, G418 selection is followed by the negative selection on colonies having 50–70 cells. Depending on the background level of resistance to the negative selection, resistant colonies are processed individually or mixed and subjected to another round of recloning and GSE selection. Inserts of GSEs are then used to identify the gene of origin by sequencing and data base comparison, by use as a probe in conventional cDNA cloning, or by use in cDNA cloning by the "anchored PCR" procedure. See Ohara et al., Proc. Natl. Acad. Sci. USA 86: 5673–5677 (1989).

EXAMPLE 10

Derivation of Anti-HIV-1 Genetic Suppressor Elements

Cloned human immunodeficiency virus-1 (HIV-1) cDNA is digested with DNase I, filled-in, fitted with linkers and size-selected, as described in Example 2. The fragment mixture is transferred into a retroviral expression vector that carries a dominant selectable marker and is capable of infecting human T cells. The HIV fragment/retroviral vector library is used to infect a human T cell line that is susceptible to killing by HIV-1 and infected cells are selected for the presence of the dominant marker. The mixture of selected cells is exposed to HIV-1, and cytopathic effect is allowed to develop to completion. Surviving cells are expanded and their DNA is isolated. DNA sequences corresponding to HIV-1 fragments are obtained by amplification of isolated cellular DNA using the polymerase chain reaction (PCR) with primers specific for the retroviral vector on either side of the insert.

PCR-generated DNA fragments are fitted with linkers and transferred to the same retroviral vector that was used to prepare the first library to create a secondary library. The same T cell line that was used for the initial library is then infected with the secondary library. Infected cells are selected for the presence of the dominant marker and individual selected clones are tested for resistance to killing by HIV-1. Resistant clones, containing putative anti-HIV-1 GSEs are used for the isolation of the putative GSE by the polymerase chain reaction, as described above. The candidate GSEs are then individually inserted into the same retroviral vector and tested for the ability to protect T-cells against cytopathic effects of HIV-1.

EXAMPLE 11

Derivation of Anti-Tobacco Mosaic Virus (TMV) Genetic Suppressor Elements

Total TMV cDNA is randomly fragmented as described in Example 2. The fragment mixture is then transferred into an expression vector containing a neomycin phosphotransferase II gene such that the inverted fragment is transcribed, initiating from the cauliflower mosaic virus 35S promoter and terminating in the polyadenylation signal from the nopaline synthase gene. Leaf disks of tobacco are inoculated with *Agrobacterium tumefaciens* cells containing the expression library. Transformed cells are selected in culture for kanamycin resistance. Kanamycin resistant cells are then exposed in culture to TMV and cytopathic effect is allowed to develop. DNA is collected from transformed TMV-resistant cells and the insert fragments are amplified by the polymerase chain reaction, using primers homologous to the DNA sequences adjacent to the insert site. Amplified sequences are transferred into the same expression vector as used to make the initial library and again used to transform *A. tumefaciens*. Tobacco leaf disks are once again inoculated with the library in *A. tumefaciens* and kanamycin-resistant cells are again tested for TMV resistance. Individual TMV-resistant clones are used for the isolation of GSEs by the polymerase chain reaction, as described above. Candidate GSEs are then used to prepare individual GSE expression vectors, which are inserted in *A. tumefaciens* to inoculate tobacco leaf disks. Inoculated leaf disks are selected for kanamycin resistant cells, from which self-pollinated individual seedlings are produced and tested for TMV resistance.

---

We claim:

1. A method for producing GSEs corresponding to recessive genes that, when inactivated by GSEs, confer a selectable or screenable phenotype upon a cell having such inactive genes, the method comprising the steps of:
   (a) obtaining genomic DNA or a total cDNA population from the cells;
   (b) randomly fragmenting the genomic DNA or total cDNA population to produce random DNA fragments;
   (c) ligating the random DNA fragments to synthetic adaptors to produce amplifiable random DNA fragments;
   (d) cloning the amplified mixture of random DNA fragments into a suitable expression vector having a selectable marker to produce a random fragment expression library;
   (e) transferring the random fragment expression library into appropriate the random fragment expression library into appropriate target cells;
   (f) selecting the target cells for the presence of the selectable marker present in the expression vector to obtain target cells having the selectable marker;
   (g) selecting or screening the target cells having the selectable marker for the selectable or screenable phenotype conferred upon the cells by inactivation of a recessive gene by a GSE;
   (h) recovering the GSE from the target cell having the selectable or screenable phenotype.

2. A method according to claim 1, wherein the target cells are mammalian cells.

3. A method according to claim 1, wherein the target cells are bacterial cells.

4. A method according to claim 1, wherein the target cells are plant cells.

5. A method according to claim 1, wherein the total cDNA population is a normalized cDNA population.

6. A method according to claim 1, wherein the GSE is a sense-oriented GSE encoding a peptide.

7. A method according to claim 1, wherein the GSE is an antisense-oriented GSE encoding an antisense RNA.

8. A method of obtaining genetic suppressor elements (GSEs) comprising the steps of:
   (a) randomly fragmenting DNA homologous to a gene to be suppressed, to yield DNA fragments;
   (b) transferring the DNA fragments to an expression vector to yield a library, wherein the expression vector is capable of expressing the DNA fragments in a living cell in which gene suppression can be selected or screened;
   (c) genetically modifying living cells by introducing the genetic suppressor elements library into the living cells;
   (d) isolating or enriching for genetically modified living cells containing genetic suppressor elements by selecting or screening for gene suppression, and;
   (e) obtaining the genetic suppressor element from the genetically modified cells.

* * * * *

UNITED STATES PATENT AND TRADEMARK OFFICE
CERTIFICATE OF CORRECTION

PATENT NO. : 6,268,134 B1
DATED : July 31, 2001
INVENTOR(S) : Roninson et al.

It is certified that error appears in the above-identified patent and that said Letters Patent is hereby corrected as shown below:

Column 1,
Line 15, insert:
-- STATEMENT OF GOVERNMENT INTEREST
This invention was made with government support under grants CA-56736-02 by the National Institutes of Health. The government has certain rights in the invention. --.

Signed and Sealed this

Twenty-eighth Day of February, 2006

JON W. DUDAS
*Director of the United States Patent and Trademark Office*

SEQUENCE LISTING

```
(1) GENERAL INFORMATION:

(iii) NUMBER OF SEQUENCES: 11

(2) INFORMATION FOR SEQ ID NO:1:

(i) SEQUENCE CHARACTERISTICS:
          (A) LENGTH: 164 base pairs
          (B) TYPE: nucleic acid
          (C) STRANDEDNESS: single
          (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO:1:

GTGTCTGGGC GGAGCAAAAT ATGTTCCAAT TGTGTTTTCT TTTGATAGAT TCTTTCAACA     60

GACAGTCTTT TCTTAGCATC TTCATTTTTC TTTATTTTGT TGACTTGCAT ATTTTCATTT    120

ACAGGCTGCA ATGGTGACAC TTCCATGGTG ACGGTCGTGA AGGG                     164

(2) INFORMATION FOR SEQ ID NO:2:

(i) SEQUENCE CHARACTERISTICS:
          (A) LENGTH: 213 base pairs
          (B) TYPE: nucleic acid
          (C) STRANDEDNESS: single
          (D) TOPOLOGY: linear (ii) MOLECULE TYPE: cDNA (iii) HYPOTHETICAL: NO
```

(iv) ANTI-SENSE: YES (xi) SEQUENCE DESCRIPTION: SEQ ID NO:2:

```
TGAAAAGATG TATGTCCCAG CTCTCATATT TGGACAGCTC CTAACTTCTA GTAACTATGA      60
TGATGATGAA AGAAAAGTGA CAGGTGGTCG AAATGGCTAT GGAGCCAAAT TGTGTAACAT     120
ATTCAGTACC AAATTTACTG TGGAAACAGC CAGTAGAGAA TACAAGAAAA TGTTCAAACA     180
GACATGGATG GATAATATGG GAAGAGCTGG TGA                                 213
```

(2) INFORMATION FOR SEQ ID NO:3:

(i) SEQUENCE CHARACTERISTICS:
        (A) LENGTH: 181 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO:3:

```
GCCCATTGGT CAGTTTGGTA CCAGGCTACA TGGTGGCAAG GATTCTGCTA GTCCACGATA      60
CATCTTTACA ATGCTCAGCT CTTTGGCTCG ATTGTTATTT CCACCAAAAC ATGATCACAC     120
GTTGAAGTTT TTATATGATG ACAACCAGCG TGTTGAGCCT GAATGGTACA TTCCTATTAT     180
T                                                                     181
```

(2) INFORMATION FOR SEQ ID NO:4:

(i) SEQUENCE CHARACTERISTICS:
        (A) LENGTH: 224 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO:4:

```
TGAATGGTAC ATTCCTATTA TTCCCATGGT GCTGATAAAT GGTGCTGAAG GAATCGGTAC      60
TGGGTGGTCC TGCAAAATCC CCAACTTTGA TGTGCGTGAA ATTGTAAATA ACATCAGGCG     120
TTTGATGGAT GGAGAAGAAC CTTTGCCAAT GCTTCCAAGT TACAAGAACT TCAAGGGTAC     180
TATTGAAGAA CTGGCTCCAA ATCAATATGT GATTAGTGGT GAAG                     224
```

(2) INFORMATION FOR SEQ ID NO:5:

(i) SEQUENCE CHARACTERISTICS:
        (A) LENGTH: 329 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO:5:

```
TGCGTGAAAT TGTAAATAAC ATCAGGCGTT TGATGGATGG AGAAGAACCT TTGCCAATGC      60

TTCCAAGTTA CAAGAACTTC AAGGGTACTA TTGAAGAACT GGCTCCAAAT CAATATGTGA     120

TTAGTGGTGA AGTAGCTATT CTTAATTCTA CAACCATTGA AATCTCAGAG CTTCCCGTCA     180

GAACATGGAC CCAGACATAC AAAGAACAAG TTCTAGAACC CATGTTGAAT GGCACCGAGA     240

AGACACCTCC TCTCATAACA GACTATAGGG AATACCATAC AGATACCACT GTGAAATTTG     300

TTGTGAAGAT GACTGAAGAA AAACTGGCA                                      329
```

(2) INFORMATION FOR SEQ ID NO:6:

(i) SEQUENCE CHARACTERISTICS:
        (A) LENGTH: 194 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO:6:

```
CACTCTTTTC AGTTTCCTTT TCGTTGTCAC TCTCTTCATT TTCTTCTTCA TCTGGAACCT      60

TTTGCTGGGC TTCTTTCCAG GCCTTCACAG GATCCGAATC ATATCCCCTC TGAATCAGAA     120

CTTTAATTAA TTCTTTCTTA GGCTTATTTT CAATGATTAT TTTGCCATCT ATTTTCTCAT     180

AGATAAAGCG AGCC                                                      194
```

(2) INFORMATION FOR SEQ ID NO:7:

(i) SEQUENCE CHARACTERISTICS:
        (A) LENGTH: 206 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO:7:

```
TCTGCCTCTG CTTTCATTTC TATGGTTATT CGTGGAATGA CTCTTTGACC ACGCGGAGAA      60

GGCAAAACTT CAGCCATTTG TGTTTTTTTC CCCTTGGCCT TCCCCCCTTT CCCAGGAAGT     120

CCGACTTGTT CATCTTGTTT TTCCTTGGCT TCAACAGCCT CCAATTCTTC AATAAATGTA     180

GCCAAGTCTT CTTTCCACAA ATCTGA                                         206
```

(2) INFORMATION FOR SEQ ID NO:8:

(i) SEQUENCE CHARACTERISTICS:
        (A) LENGTH: 194 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO:8:

```
GACACGACAC TTTTCTGTGG TTTCAGTTCT TTGTTACTAA GTTTTGGGGA AGTTTTGGTC      60

TTAGGTGGAC TAGCATCTGA TGGGACAAAA TCTTCATCAT CAGTTTTTTC ATCAAAATCT     120

GAGAAATCTT CATCTGAATC CAAATCCATT GTGAATTTTG TTTTTGTTGC TGCTCTCCGT     180

GGCTCTGTTT CTCG                                                       194
```

(2) INFORMATION FOR SEQ ID NO:9:

(i) SEQUENCE CHARACTERISTICS:
        (A) LENGTH: 242 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO:9:

```
CTGAAACCAC AGAAAAGTGT CGTGTCAGAC CTTGAAGCTG ATGATGTTAA GGGCAGTGTA      60

CCACTGTCTT CAAGCCCTCC TGCTACACAT TTCCCAGATG AAACTGAAAT TACAAACCCA     120

GTTCCTAAAA AGAATGTGAC AGTGAAGAAG ACAGCAGCAA AAAGTCAGTC TTCCACCTCC     180

ACTACCGGTG CCAAAAAAAG GGCTGCCCCA AAAGGAACTA AAAGGGATCC AGCTTTGAAT     240

TC                                                                    242
```

(2) INFORMATION FOR SEQ ID NO:10:

(i) SEQUENCE CHARACTERISTICS:
        (A) LENGTH: 220 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO:10:

```
AATTCAAAGC TGGATCCCTT TTAGTTCCTT TTGGGGCAGC CCTTTTTTTG GCACCGGTAG      60

TGGAGGTGGA AGACTGACTT TTTGCTGCTG TCTTCTTCAC TGTCACATTC TTTTTAGGAA     120

CTGGGTTTGT AATTTCAGTT TCATCTGGGA AATGTGTAGC AGGAGGGCTT GAAGACAGTG     180

GTACACTGCC CTTAACATCA TCAGCTTCAA GGTCTGACAC                            220
```

(2) INFORMATION FOR SEQ ID NO:11:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (xi) SEQUENCE DESCRIPTION: SEQ ID NO:11:

```
CATGGTGACT GACTGAAGCT                                                  20
```